United States Patent [19]

Martan et al.

[11] Patent Number: 5,144,091
[45] Date of Patent: Sep. 1, 1992

[54] PREPARATION OF ACROLEIN OR METHACROLEIN BY CATALYTIC GAS-PHASE OXIDATION OF PROPENE OR ISOBUTENE

[75] Inventors: Hans Martan, Frankenthal; Ulrike Wegerle, Worms; Wilhelm Ruppel, Schwetzingen; Lothar Riekert, Karlsruhe; Dieter Becker, Sulzbach a. T.; Michael Kotter, Bruchsal, all of Fed. Rep. of Germany

[73] Assignee: BASF Aktiengesellschaft, Ludwigshafen, Fed. Rep. of Germany

[21] Appl. No.: 732,910

[22] Filed: Jul. 19, 1991

[30] Foreign Application Priority Data

Jul. 21, 1990 [DE] Fed. Rep. of Germany ....... 4023239

[51] Int. Cl.$^5$ .............................................. C07C 45/35
[52] U.S. Cl. ................................... 568/479; 568/470; 568/475; 568/476
[58] Field of Search ............... 568/449, 470, 475, 476, 568/482, 479

[56] References Cited

U.S. PATENT DOCUMENTS 3,801,634  4/1974  Krabetz et al. ....................... 568/476
4,837,360  6/1989  Kadowaki et al. .................. 568/482

FOREIGN PATENT DOCUMENTS 2056614  6/1972  Fed. Rep. of Germany ...... 568/476
2513405  10/1976  Fed. Rep. of Germany ...... 568/476
2611249  11/1976  Fed. Rep. of Germany .
3006894  9/1980  Fed. Rep. of Germany ...... 568/476

*Primary Examiner*—Werren B. Lone
*Attorney, Agent, or Firm*—Oblon, Spivak, McClelland, Maier & Neustadt

[57] ABSTRACT

A process for the catalytic gas-phase oxidation of propene or isobutene to acrolein or methacrolein in a tubular fixed bed reactor or catalytically active oxides with a $\geq 90\%$ conversion of the initial olefin on a single passage, wherein the temperature of the gases containing the reactants in the direction of flow along the tubes from their entrance until the conversion of the initial olefin is from 30 to 70% is from 360° to 420° C. and is then adjusted to from 360° to 300° C. until the conversion of the initial olefin is from 80 to 90% and is thereafter maintained at from 330° to 390° C. until the gases emerge from the tubes, is described.

2 Claims, No Drawings

PREPARATION OF ACROLEIN OR METHACROLEIN BY CATALYTIC GAS-PHASE OXIDATION OF PROPENE OR ISOBUTENE

The present invention relates to a novel process for the catalytic gas-phase oxidation of propene or isobutene to acrolein or methacrolein in a tubular fixed bed reactor at elevated temperatures on catalytically active oxides with a $\geq 90\%$ conversion of the initial olefin on a single passage.

The gas-phase oxidation of propene or isobutene to acrolein or methacrolein is particularly important as the first oxidation stage in the preparation of acrylic or methacrylic acid by two-stage catalytic gas-phase oxidation of propene or isobutene.

It is a very exothermic reaction, which is why it is necessary, because of the large number of possible parallel or secondary reactions, to control the temperature profile to maximize the selectivity of the conversion of propene into acrolein and of isobutene into methacrolein.

DE-C 25 13 405 discloses the control of the temperature profile in the catalytic gas-phase oxidation of propene to acrolein in a multiple-tube fixed bed reactor on catalytically active oxides with propene conversions of at least 90% on a single passage in such a way that a molten salt at 330° C. circulates through the space surrounding the tubes, and the mixture containing the reactants is preheated to 330° C. before being passed into the reaction zone. DE-A 20 56 614 and DE-A 30 06 894 additionally influence the temperature profile in the catalytic gas-phase oxidation of propene to acrolein by increasing the activity of the catalyst composition by dilution with inert material and by altering the composition in the direction of flow, respectively. However, the disadvantage of these processes is that the implicit temperature profiles along the tubes is not entirely satisfactory with a view to maximizing the selectivity of the conversion of the initial olefin into the aldehyde.

It is an object of the present invention to provide a process for the catalytic gas-phase oxidation of propene or isobutene to acrolein or methacrolein in a tubular fixed bed reactor at elevated temperatures on catalytically active oxides with a $\geq 90\%$ conversion of the initial olefin on a single passage, which has an improved temperature profile so as to increase the selectivity of aldehyde formation.

We have found that this object is achieved by a process for the catalytic gas-phase oxidation of propene or isobutene to acrolein or methacrolein in a tubular fixed bed reactor at elevated temperatures on catalytically active oxides with a $\geq 90\%$ conversion of the initial olefin on a single passage, wherein the temperature of the gases containing the reactants in the direction of flow along the tubes from their entrance until the conversion of the initial olefin is from 30 to 70% is from 360° C. to 420° C. and is then adjusted to from 360° C. to 300° C. until the conversion of the initial olefin is from 80 to 90% and is thereafter maintained at from 330° C. to 390° C. until the gases emerge from the tubes.

Particularly suitable catalytic oxides are compositions of the formula I $$Mo_{12}Bi_aFe_bX^1_cX^2_dX^3_eX^4_fO_n \qquad (I)$$

where $X^1$ is nickel or cobalt, $X^2$ is thallium, an alkali metal or an alkaline earth metal, $X^3$ is phosphorus, arsenic, boron, antimohy, tin, cerium, lead, niobium or tungsten, $X^4$ is silicon, aluminum, titanium or zirconium, a is from 0.5 to 5.0, b is from 0.01 to 3.0, c is from 3.0 to 10.0, d is from 0.02 to 2.0, e is from 0 to 5.0, f is from 0 to 10 and n is determined by the valency and content of the elements different from oxygen in I.

Particularly preferred compositions have the formula $Mo_{12}Bi_1Fe_2Ni_{8.5}P_{0.06}Na_{0.18}K_{0.06}Si_{10}O_n$ (for the oxidation of propene to acrolein) and the formula $Mo_{12}Bi_1Fe_3Ni_1Co_7B_2Sb_{0.1}K_{0.14}O_n$ (for the oxidation of isobutene to methacrolein).

Compositions I can be obtained in a conventional manner. They can be prepared, for example, by mixing solutions or suspensions of suitable salts of the elements constituting them, with or without raising the temperature and adding acids or bases, in aqueous medium, evaporating the mixture to dryness, shaping the resulting composition and calcining it, usually at from 180° C. to 480° C., preferably 350° C. to 450° C., in a stream of air or in an inert atmosphere, eg. $N_2$ or $CO_2$. It is possible to add conventional auxiliaries for the shaping, such as lubricants (eg. graphite) or shaping auxiliaries and reinforcers such as microfilaments of glass, asbestos, silicon carbide or potassium titanate. The compositions I are expediently prepared in this form for use as unsupported catalysts, in which case the preferred geometry is a hollow cylinder with an external diameter and a length of from 4 to 10 mm and a wall thickness of from 1 to 3 mm. However, the catalytically active oxides can also be used in the form of coated catalysts, ie. applied to preshaped carrier materials, in which case the catalyst can be applied in the form of an aqueous solution or suspension, for example, to the carrier material, followed by drying and calcination, or in the form of a calcined and powdered composition combined with a binder.

It is of course also possible for the catalytically active compositions to be employed in powder form as catalysts.

The oxygen for the oxidation can be, for example, in the form of air or else in pure form. The reactants are preferably diluted with inert gas such as $N_2$, recycled gases from the reaction and/or steam. The ratio of initial olefin to oxygen to inert gases (including steam) is usually 1:1.0-3.0:5-25, preferably 1:1.7-2.3:10-15, by volume in 1(STP). The pressure is normally in the range from 1 to 3 bar and the overall material flow is preferably from 1500 to 2500 1(STP)/l/h. The described process results not in pure acrolein or methacrolein but in a gas mixture from which acrolein or methacrolein can be separated in a conventional manner. When the acrolein or methacrolein is used for the preparation of acrylic or methacrylic acid by two-stage catalytic gas-phase oxidation of propene or isobutene, the gases containing acrolein or methacrolein are usually passed through to the second oxidation stage without removing the other components.

The temperature profile according to the invention can be achieved in a conventional manner, eg. by heating or cooling sections of the tube with electric heating tapes or circulating fluid media such as molten salts, such as potassium nitrate, sodium nitrite and/or sodium nitrate, or fusible metals such as sodium, mercury or alloys of various metals, it being the case that, with a single tube, because of the efficient heat transfer the temperature inside the tube during the reaction is essentially the same as the outside temperature.

However, heating or cooling of sections is also possible with multiple-tube fixed bed reactors and is described, for example, in DE-A 28 30 765, DE-A 22 01 528, DE-A 16 01 162, DE-A 25 13 405 and US-A 3 147 084. Another possibility for controlling the reaction temperature comprises increasing or decreasing the catalyst activity in sections. This can be achieved by chemical modification of the active catalyst composition or else by dilution with inactivated catalyst or inert material (DE-A 20 56 614 and DE-A 30 06 894).

It is also possible to combine sectional heating/cooling with sectional increases/decreases in catalyst activity. The initial gases are preferably always preheated to the appropriate temperature before entering the first reaction zone.

Typical tubes are composed of stainless steel with a wall thickness of about 2 mm and an internal diameter of 25 mm. The number of tubes in a multiple-tube fixed bed reactor is usually from 10,000 to 30,000. The conversion C and selectivity S are defined as follows:

$$C = \frac{\text{no. of moles of propene reacted}}{\text{no. of moles of propene fed in}} \times 100$$

$$S = \frac{\text{no. of moles of propene converted into acrolein}}{\text{total no. of moles of propene reacted}} \times 100$$

EXAMPLE E and COMPARATIVE EXAMPLE C

E: A steel tube (stainless, wall thickness 2 mm, internal diameter 25 mm) heated in sections with electric heating tapes was packed to a height of 2.5 m with coated catalyst of Example 4a) of EP-B 17 000, and a gas mixture of the composition

| |
|---|
| 5% by volume propene |
| 45% by volume air and |
| 50% by volume nitrogen | which had been preheated to 380° C. was passed through at 1800 1/1/h. The tube was maintained at 380° C. up to a propene conversion of 65%, and then the temperature along the tube was reduced to 335° C. up to a propene conversion of 85% and subsequently maintained at 340° C. up to the exit from the tube. The propene conversion C with a single passage was 95% and the selectivity S of acrolein formation was 93%.

C: The procedure of E was used except that the gas mixture was preheated to 350° C. and the temperature along the whole of the tube was maintained at 350° C. The propene conversion C with a single passage was likewise 95% while the selectivity S of acrolein formation was 88%.

We claim:

1. A process for the production of acrolein or methacrolein by catalytic gas-phase oxidation of propene or isobutene by a molecular oxygen-containing gas in a tubular fixed bed reactor at elevated temperatures on catalytically active oxides with a ≧90% conversion of the initial olefin on a single passage, wherein the temperature of the gases containing said oxygen-containing gas and either of propene or isobutene in the direction of flow along the tubes from their entrance until the conversion of the initial olefin is from 30 to 70% is from 360° C. to 420° C. and is then adjusted to from 360° C. to 300° C. until the conversion of the initial olefin is from 80 to 90% and is thereafter maintained at from 330° C. to 390° C. until the gases emerge from the tubes.

2. A process as claimed in claim 1, wherein the catalytic oxides are compositions of the formula $$Mo_{12}Bi_aFe_bX^1_cX^2_dX^3_eX^4_fO_n \qquad (I)$$

where $X^1$ is nickel or cobalt, $X^2$ is thallium, an alkali metal or an alkaline earth metal, $X^3$ is phosphorus, arsenic, boron, antimohy, tin, cerium, lead, niobium or tungsten, $X^4$ is silicon, aluminum, titanium or zirconium, a is from 0.5 to 5.0, b is from 0.01 to 3.0, c is from 3.0 to 10.0, d is from 0.02 to 2.0, e is from 0 to 5.0, f is from 0 to 10 and n is determined by the valency and content of the elements different from oxygen in I.

* * * * *